United States Patent
Ikhlef

(10) Patent No.: US 8,699,659 B2
(45) Date of Patent: Apr. 15, 2014

(54) SYSTEMS AND METHODS FOR FOCAL SPOT MOTION CORRECTION

(75) Inventor: Abdelaziz Ikhlef, Hartland, WI (US)

(73) Assignee: General Electric Company, Schenectady, NY (US)

( * ) Notice: Subject to any disclaimer, the term of this patent is extended or adjusted under 35 U.S.C. 154(b) by 177 days.

(21) Appl. No.: 13/166,987

(22) Filed: Jun. 23, 2011

(65) Prior Publication Data
US 2012/0328076 A1   Dec. 27, 2012

(51) Int. Cl.
*G01N 23/04* (2006.01)

(52) U.S. Cl.
USPC .................................................. 378/19; 378/7

(58) Field of Classification Search
USPC ............................................ 378/19, 7, 13, 20
See application file for complete search history.

(56) References Cited

U.S. PATENT DOCUMENTS

| | | | |
|---|---|---|---|
| 6,092,928 A | 7/2000 | Mattson et al. | |
| 6,327,331 B1 | 12/2001 | Toth et al. | |
| 6,359,958 B2 | 3/2002 | Toth | |
| 7,609,804 B2 | 10/2009 | Hoffman | |
| 2004/0120464 A1 | 6/2004 | Hoffman | |
| 2010/0046709 A1* | 2/2010 | Ueki | 378/98 |

* cited by examiner

*Primary Examiner* — Hoon Song
(74) *Attorney, Agent, or Firm* — The Small Patent Law Group; Dean D. Small

(57) ABSTRACT

Systems and methods for focal spot motion correction are provided. One system includes a radiation source configured to project radiation from a first focal spot onto an object and a plurality of radiation detectors disposed around at least a portion of the object. The plurality of radiation detectors measure received radiation along a path projected from the first focal spot to the plurality of detectors. The imaging system further includes an imaging region from which the detectors provide image information for image reconstruction and a plurality of collimators positioned between the object and the plurality of radiation detectors. At least one collimator at a first end of the plurality of collimators and at least one collimator at second end of the plurality of collimators are aligned to a second focal spot different than the first focal spot and having a different location.

24 Claims, 6 Drawing Sheets

SYSTEMS AND METHODS FOR FOCAL SPOT MOTION CORRECTION

BACKGROUND OF THE INVENTION

The subject matter disclosed herein relates generally to imaging systems, and more particularly to correcting focal spot motion induced errors in detectors of the imaging systems.

Some known imaging systems, such as Computed Tomography (CT) imaging systems, include a source and a detector array as part of a gantry. The source and the detector rotate with the gantry within an imaging plane and around an object to be imaged such that the angle at which the beam intersects the object constantly changes. A scan of the object includes acquiring a set of views at different gantry angles, or view angles, during one revolution of the source and detector. In an axial scan, the projection data is processed to construct an image that corresponds to a two dimensional slice taken through the object. The reconstruction process then converts the attenuation measurements from a scan into integers called "CT numbers" or "Hounsfield units", which are used to control the brightness of a corresponding pixel on a display.

In these imaging systems, the focal spot is the region from which the radiation projects. In some systems, the radiation produced diverges from the focal spot in a conical pattern. In order to produce an image from an axial scan with acceptable resolution, such as to provide clinically relevant image details, it is desirable for the focal spot to be properly aligned in the x-axis.

In particular, during operation, these imaging systems heat up due to different factors. The heat causes a thermal expansion of the some of the radiation source structures. The thermal expansion causes small mechanical displacements of source structures and a corresponding shift in the focal spot position. To correct for this shift, at least one known imaging system aligns the source at a single temperature, for example, an ambient temperature. However, as a result of the thermal drift, the single temperature alignment does not accurately reflect the position of the source focal spot during a scan of an object. The thermal drift of the focal spot then can cause aliasing and reduced image quality.

Focal spot drift may also result from the rotation of the gantry relative to the object being scanned, caused by the methods used for imaging system calibration, such as air calibration, misalignment of mechanical parts, and oscillation of the focal spot due to mechanical vibrations, among others. Thus, because perfect mechanical alignment of the focal spot is difficult or impossible to achieve in a commercial production setting and difficult to maintain in a clinical setting, systems and methods to mitigate focal spot motion/drift are used.

SUMMARY OF THE INVENTION

In accordance with one embodiment, an imaging system is provided that includes a radiation source configured to project radiation from a first focal spot onto an object and a plurality of radiation detectors disposed around at least a portion of the object. The plurality of radiation detectors measure received radiation along a path projected from the first focal spot to the plurality of detectors. The imaging system further includes an imaging region from which the detectors provide image information for image reconstruction and a plurality of collimators positioned between the object and the plurality of radiation detectors. At least one collimator at a first end of the plurality of collimators and at least one collimator at second end of the plurality of collimators are aligned to a second focal spot (e.g., a second focal point location) different than the first focal spot location and having a different location.

In accordance with another embodiment, a method to track focal spot motion is provided. The method includes configuring a radiation source to project radiation from a first focal spot (e.g., a real focal spot) onto an object and configuring a plurality of radiation detectors to surround at least a portion of the object. The plurality of radiation detectors measure received radiation along a path projected from the first focal spot to the plurality of detectors, wherein an imaging region from which the detectors contribute intensity for image reconstruction is defined. The method also includes providing a plurality of collimators between the object and the plurality of radiation detectors, wherein at least one collimator at the first end of the plurality of collimators and at least one collimator at a second end of the plurality of collimators are aligned to a second focal spot (e.g., a virtual focal spot), with the first focal spot being different than the second focal spot.

In accordance with yet another embodiment, a non-transitory computer readable storage medium for tracking a focal spot of a detector using a processor is provided. The non-transitory computer readable storage medium includes instructions to command the processor to realign the collimation of at least one collimator at a first end of a plurality of collimators and at least one collimator at a second end of the plurality of collimators, such that the collimators at the first and second ends are aligned to a focal spot (e.g., a focal point) different than the other ones of the plurality of collimators.

BRIEF DESCRIPTION OF THE DRAWINGS

The drawings illustrate generally, by way of example, but not by way of limitation, various embodiments discussed in the present document.

DETAILED DESCRIPTION OF THE INVENTION

Figure 1:
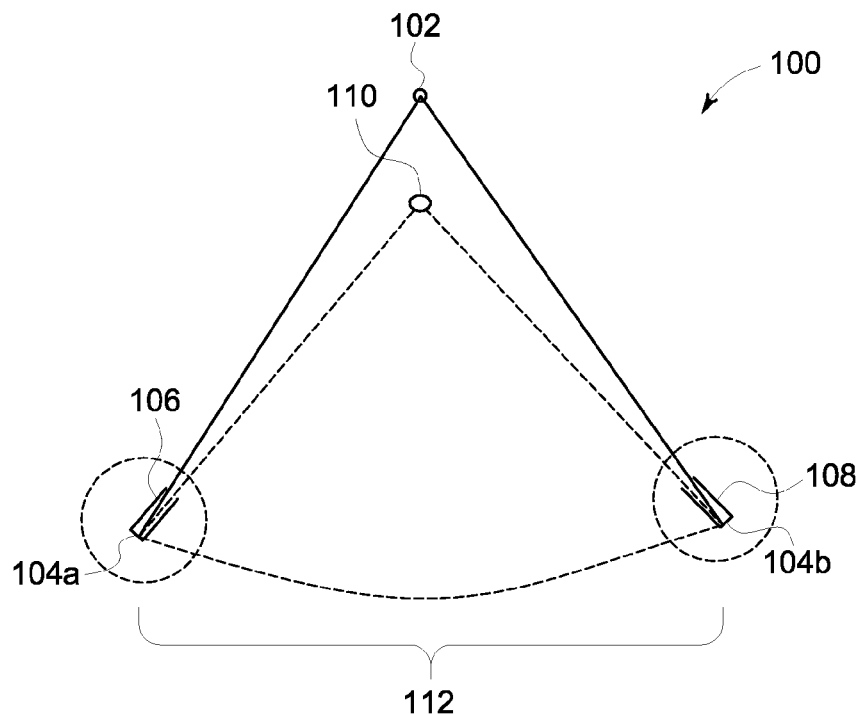
FIG. 1 is a diagram illustrating focal spot tracking using one or more end collimators in accordance with an embodiment.

The foregoing summary, as well as the following detailed description of certain embodiments of the subject matter set forth herein, will be better understood when read in conjunction with the appended drawings. As used herein, an element or step recited in the singular and proceeded with the word "a" or "an" should be understood as not excluding plural of said elements or steps, unless such exclusion is explicitly stated. In this document, the term "or" is used to refer to a nonexclusive or, unless otherwise indicated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

In the following detailed description, reference is made to the accompanying drawings which form a part hereof, and in which are shown by way of illustration specific embodiments in which the subject matter disclosed herein may be practiced. These embodiments, which are also referred to herein as "examples," are described in sufficient detail to enable those skilled in the art to practice the subject matter disclosed herein. It is to be understood that the embodiments may be combined or that other embodiments may be utilized, and that structural, logical, and electrical variations may be made without departing from the scope of the subject matter disclosed herein. The following detailed description is, therefore, not to be taken in a limiting sense, and the scope of the subject matter disclosed herein is defined by the appended claims and their equivalents. In the description that follows, like numerals or reference designators will be used to refer to like parts or elements throughout.

Various embodiments provide focal spot tracking using one or more end collimators. It should be noted that various embodiments include systems and methods (implemented in hardware, software, or a combination thereof) that can be used to correct or compensate for focal spot motion induced errors and provide a normalization reference to track the intensity of the moving focal spot.

As used herein, a focal spot generally refers to a region from which one or more radiations project. For example, a focal spot may be a region on an anode of an X-ray tube, wherein the X-ray tube forms part of an X-ray imaging systems, such as a projection radiography system and/or Computed Tomography (CT) system.

It should be noted that the focal spot, when viewed along the central radiation beam in a field, is commonly shaped as a square. The size of the focal spot may be, for example, 0.6× 0.6 mm². However, the actual focal spot on the anode in various embodiments may take different shapes, for example, rectangular. As the anode is angled, the square view of focal spot when projected back on the anode has an elongated edge. Thus, the size of focal spot influences the spatial resolution of imaging system, such that the smaller the focal spot, the higher the limiting spatial resolution. Additionally, geometric sharpness may be affected by focal spot motion, which depends on the location of the scanned object relative to the focal spot and the detector receiving the projection. By practicing at least some embodiments, one technical effect is that the motion of the focal spot that limits spatial resolution and affects the geometric sharpness of the imaging system may be corrected or reduced.

Also, as used herein, a focal spot range generally refers to a sum of a maximum displacement of the focal spot from the original position in either direction in one dimension, such that a ray of radiation emanating from the focal spot can be directly received by the detector. If the focal spot motion occurs, for example in x-axis, the collimator and detector may become defocused. When such defocusing occurs, all of the detectors in the channels view the same range of detector gain variation. Hence, when the ratio of these gains between alternate channels is calculated, the ratio may always be 1 as there is no variation between individual channels. The ratio of 1 may result because all channels have the same defocusing due to focal spot motion. By practicing at least some embodiments, detector with higher gain may be provided with the gain affected less by focal spot motion. Thus, in various embodiments, defocusing of end collimators is used for focal spot motion tracking.

Referring now to FIG. 1, an image acquisition portion 100 of an imaging system (e.g., a CT system) include a plurality of detectors 104, a plurality of collimators (a pair of end collimators 106 and 108 at first and second ends are shown), and a focal spot 102. It should be noted that the focal spot 102 may be, for example, a focal point, a focal area, a focal region and the like, generated by an X-ray source (not shown in FIG. 1). The image acquisition portion 100 may be used to provide focal spot tracking as described herein. The detectors 104 and collimators (such as collimators 106 and 108) may be provided, for example, as a plurality of modules. As used herein, the imaging area or imaging region 112 is generally defined as the area/region that contributes intensity data to be displayed in an image. Additionally, as used herein, a channel generally refers to a space between two adjacent collimator plates, providing a passage for the radiation to reach the detectors 104. Also, the collimators may be configured to protect the detectors 104 from receiving background radiation that may add noise to the images generated using the imaging system.

The collimators in the imaging region 112 are aligned to the focal spot 102 or the focal spot 110 as described in more detail herein. In one embodiment, the detectors 104a and 104b are aligned to point or focus to a virtual focal spot, illustrated as the focal spot 110, using the end collimators 106 and 108 as described in more detail herein.

It should be noted that the height of the collimators, including the collimators 106 and 108 may be varied. For example, the height of the collimators may be determined based on scatter-to-primary rejection ratio, for example, a ratio of background scatter to the actual radiation received by the detectors. As used herein, the x-axis refers to the axis that is perpendicular to the collimator length.

Although, the increased coverage in imaging systems, for example, in CT imaging systems, provides increased diagnostic confidence that more area is scanned, as well as assisting in locating diagnostic information that may be missed with smaller scanning area, the noise from scattered radiation is also multiple times higher. For example, the noise for a 160 mm coverage area may be 4 times higher than when the coverage area is 40 mm. Thus, as a result in the increase in scatter noise, the collimator height may be increased, to compensate for this scatter.

In order to correct or compensate for mis-alignment and/or focal sport drift, various embodiments provide an arrangement that is focused to two different focal points, which in the illustrated embodiments are pints defined by the focal spots 102 and 110, which may be referred to as the real focal spot and the virtual focal spot, respectively.

In various embodiments, to correct or compensate for focal spot motion (which may cause penumbra and gain variation between neighboring channels), focal spot tracking is performed using the end collimators 106 and 108, which in one embodiment, are the collimators at opposite ends of the collimator assembly within the imaging region 112. In one embodiment, the end collimators 106 and 108 is defocused and aligned with the focal spot 110, with the other collimators, namely the collimators for the detectors between the end collimators 106 and 108, focused and aligned on the focal spot 102. It should be noted that the defocusing of the end collimators 106 and 108 may be performed in hardware, for example, by physically tilting the end collimators 106 and 108 or in software, by realigning the data received from the focal spot 102 to the focal spot 110.

Thus, the defocusing of the end collimators 106 and 108 in various embodiments includes aligning the end collimators 106 and 108 to the focal spot 110 from the focal spot 102. It should be noted that the focal spot 110 is a (defocused) virtual focal point and the focal spot 102 is a real focal spot. In one embodiment, the end collimators 106 and 108 may result in defocusing of the first and last few channels or modules by a fixed angle in opposite directions. For example, the end collimators 106 and 108, which may be the first and last few collimators, may be defocused by a fixed angle in opposite directions, such as skewed by 3 minutes angle. For example, the left side end collimator 106 (as viewed in FIG. 1) may be skewed by +3 minutes and the right end collimator 108 (as viewed in FIG. 1) may be skewed by −3 minutes.

It should be noted that the defocused end collimators 106 and 108 still receive radiation from the focal spot 102. For example, the amount of radiation received by the defocused end collimators 106 and 108 may be 90% of the amount of radiation that passes through a focused and aligned collimator (i.e., aligned with the focal spot 102). If the focal spot moves left of the center position, the detector 104a on the left end, having the defocused collimator 106, will see an increase in the radiation signal received. On the other end, the detector 104b on the right end, having the defocused collimator 108, will see a decrease in the radiation signal received.

Defocusing the end detectors 104a and 104b using collimation, such as physical defocusing of the collimators 106 and 108 generates a reference channel that is less sensitive or insensitive to motion of the focal spot 102. Additionally, defocusing of the end collimators 106 and 108 provides a measurement of the focal spot drift/motion from the alignment position more accurately. The measurement of focal spot drift may be used to calibrate the focal spot 102. Also, the measurement of focal spot drift may be used to normalize detector gain.

Figure 2:
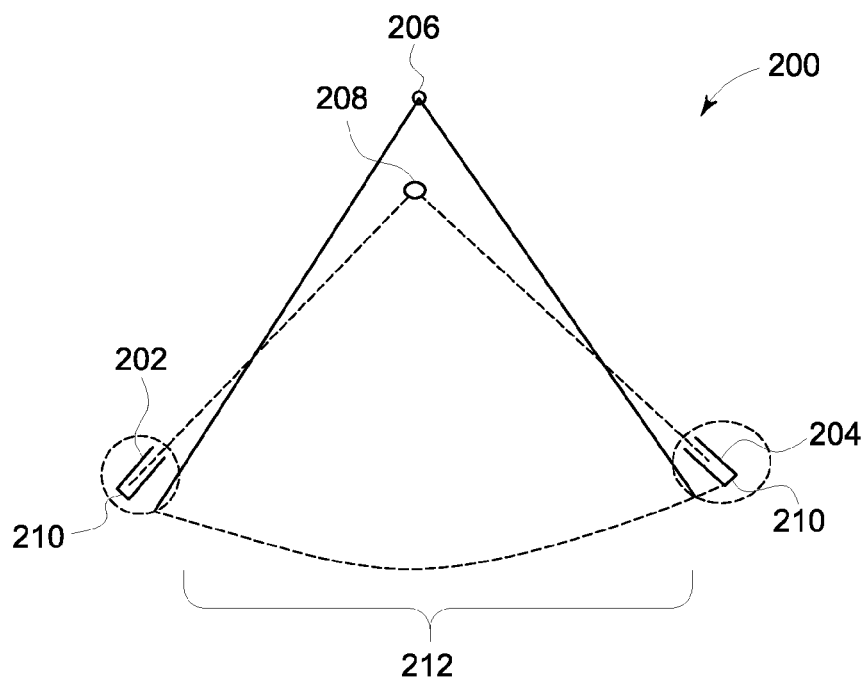
FIG. 2 is a diagram illustrating focal spot tracking using one or more additional collimators and a sensor pairs in accordance with an embodiment.

FIG. 2 illustrates an image acquisition portion 200 that also may provide focal spot tracking. In this embodiment, the image acquisition portion 200 provides focal spot tracking using additional collimators 202 and 204 in combination with detectors 210 that are added to the ends of the imaging region 212. In this embodiment, similar to the embodiment of FIG. 1, all of the collimators in the imaging region 212 are aligned to a focal spot 206 (also referred to as a focal spot position) and the additional collimator pairs 202 and 204 at the end of the collimator assembly are defocused and aligned to the focal spot 208, illustrated as a virtual focal point. The detectors 210 having collimators 202 and 204, in various embodiments, do not provide image information, such as intensity information, for image reconstruction, but are used only for focal spot motion tracking. However, it should be noted that optionally the detectors 210 provided with the collimators 202 and 204 may provide intensity information.

Figure 3:
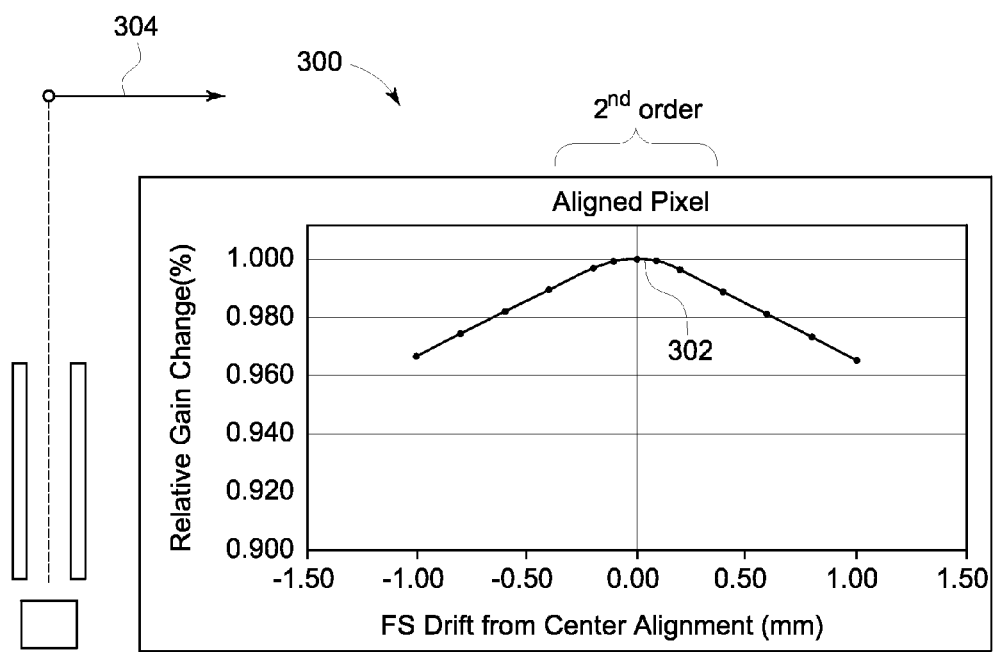
FIG. 3 is a graph illustrating the relationship of gain variation and focal spot drift without focal spot tracking.

FIG. 3 is a graph 300 illustrating the relationship of gain variation and focal spot drift without focal spot tracking. In particular, the graph 300 illustrates the relationship of gain variation and focal spot drift when the collimators are aligned to the real focal spot position. When focal spot tracking collimators are not used, and the collimators in the image space are aligned to the original focal spot position, the gain graph is represented by a generally parabolic curve. Hence, when the focal spot is at the center of the aligned collimators, the curve of the parabola is at the highest point 302 and has a relative gain variation of 1. However, when the focal spot moves either to left or right (illustrated by the arrow 304) of the center alignment position, the gain for each channel decreases rapidly. As can be seen, the gain varies as the focal spot moves from the aligned position. Beyond a certain angle, the gain varies linearly. It should be noted that in the aligned position, the gain can be modeled with a second order polynomial function.

Figure 4:
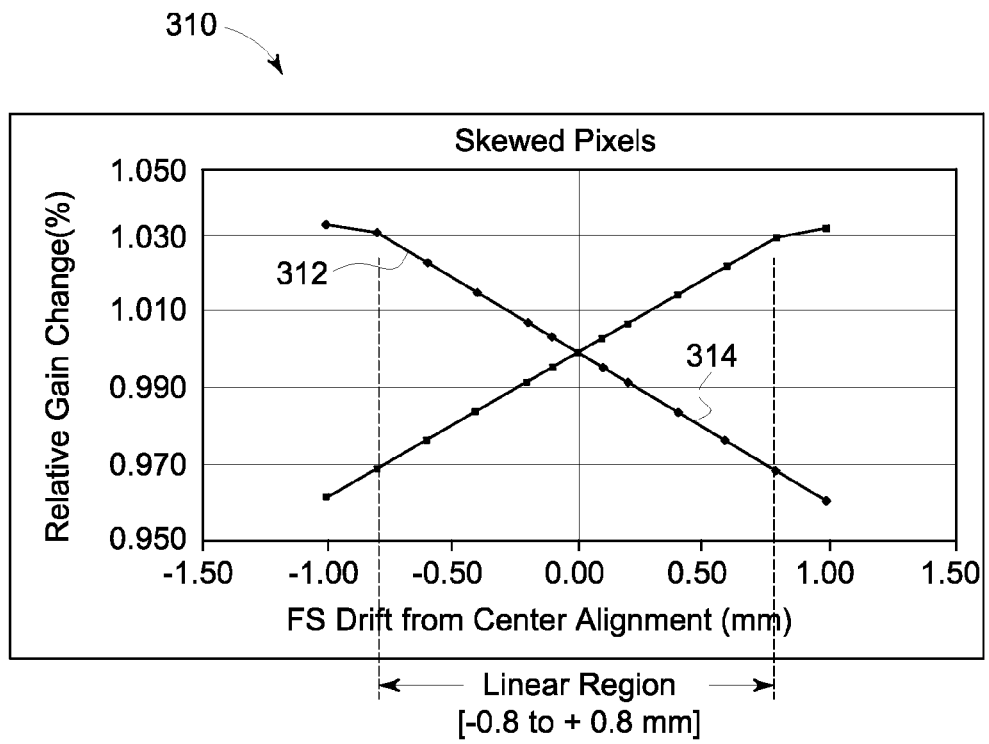
FIG. 4 is a graph illustrating the relationship of gain variation and focal spot drift with focal spot tracking in accordance with an embodiment.

FIG. 4 is a graph 310 illustrating the relationship of a gain variation and a focal spot drift with focal spot tracking performed in accordance with one or more embodiments. The graph 310 illustrates the relationship of a gain variation and a focal spot drift calculated as a function of the focal spot motion using the collimators misaligned to the real focal spot position (e.g., collimators focused or pointed to a virtual focal spot). The graph 310 shows the relationship of a gain variation and a focal spot drift with focal spot tracking with the end collimators skewed by +/−3 minutes, as illustrated by the lines 312 and 314. The gain variation for radiation received at the detector using the +/−3 minutes skewed collimator is linear. In this example, the left channel collimator is skewed by −3 min and the right channel collimator is skewed by +3 min. The point of intersection of the gain curve and the linear region is dependent on the value of collimator skew.

Figure 5:
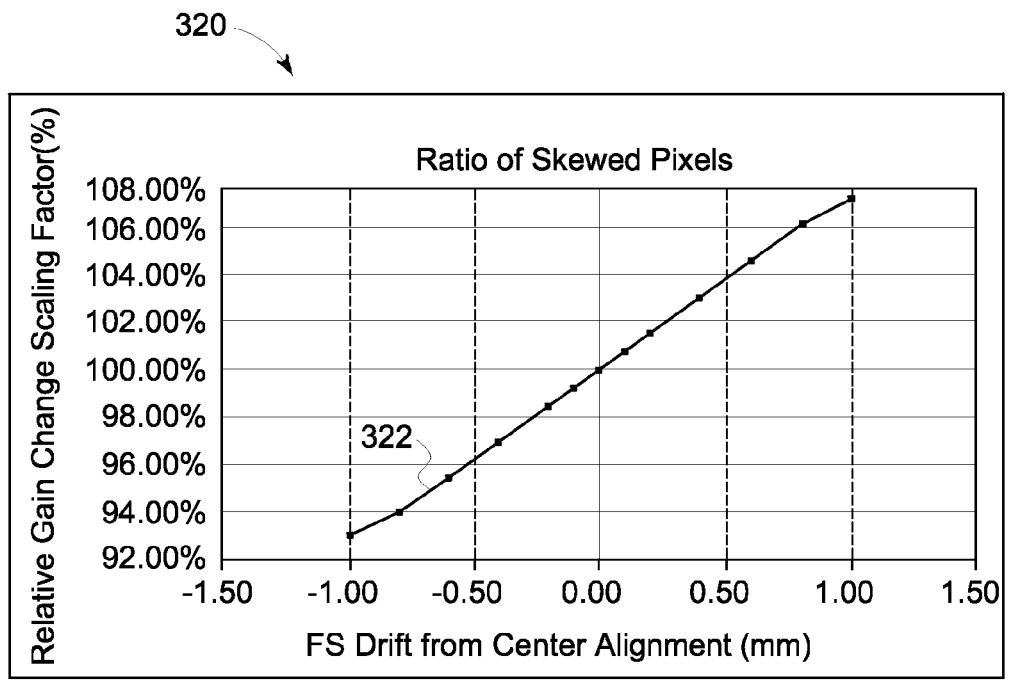
FIG. 5 is another graph illustrating the relationship of gain ratio variation and focal spot drift with focal spot tracking in accordance with an embodiment.

FIG. 5 is a graph 320 showing the relationship of a gain ratio variation and focal spot drift with focal spot tracking in accordance with an embodiment. In particular, the graph 320 illustrates the relationship of a gain ratio variation and focal spot drift detected using the detectors that are focused to a virtual focal spot position (e.g., defocused from the real focal spot position), for example, two detectors that are oppositely misaligned from the real focal spot. The graph 320 shows the relationship of a gain ratio variation and focal spot drift (in line 322) with focal spot tracking with the end collimators skewed by +/−3 minutes. Thus, because the gain ratio of the skewed pixels can be modeled by a linear curve fitting, the implementation of calibration can be simplified.

In particular, when the focal spot in at the original position, namely without any motion, the two skewed end collimated detectors register the same relative intensity for the radiation received from the focal spot. When the focal spot drifts or moves, the ratio of the gain variation for the right and the left skewed channel provides a substantial linear region. Hence, the intensities detected by each channel are substantially the same in the linear region.

Figure 6:
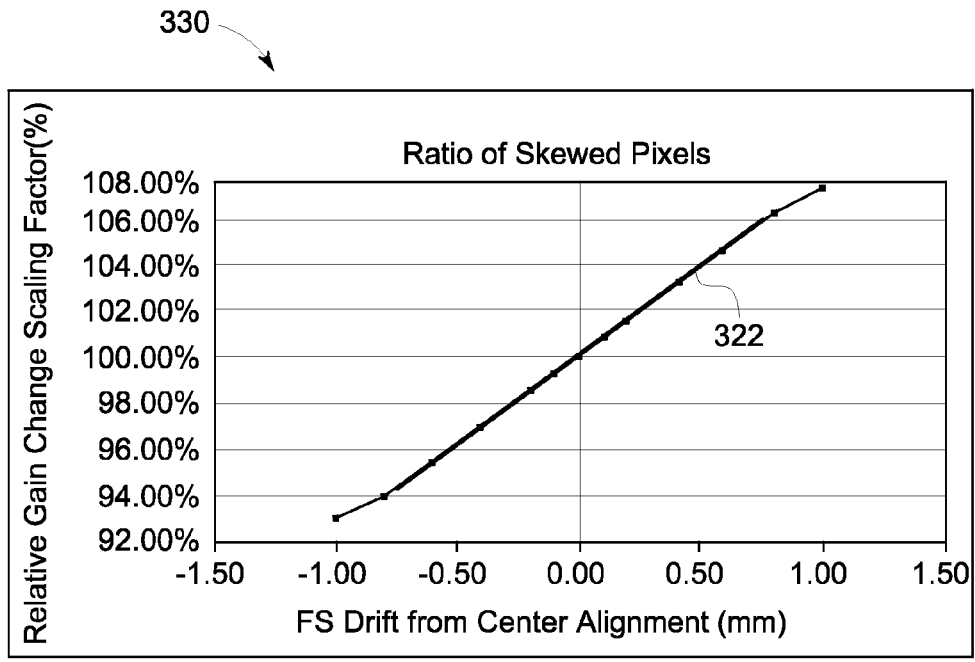
FIG. 6 is a graph showing a region of the graph of FIG. 5 used for calculating a linear relationship between a scaling factor and focal spot drift.

FIG. 6 is a graph 330 showing a region of the graph 320 of FIG. 5 (namely a portion of the line 322) used for calculating a linear relationship between scaling factor and focal spot drift. The linear relationship may be calculated, for example, as follows:

$$\text{Scaling Factor} = a \cdot x + b$$

where x is FS position $$FS_{position} = \frac{(\text{Ratio} - b)}{a}$$

An average reference channel as the focal spot intensities are tracked may be represented as follows:

$$\text{Ratio} = \frac{\text{Gain\_ch\_positive skew}}{\text{Gain\_ch\_negative skew}}$$

The method for calculating the calibration includes measuring positive and negative skew ratios, then using the measured ratio to calculate calibration coefficients, which provides a linear equation of the gain as a function of the ratio. The linear equation can be used to calibrate every scan to the second focal spot position or defocused focal spot position as described herein. In the graph, the 0 on the x-axis is the second focal spot position center (e.g., the focal spot 110 or 208 in FIGS. 1 and 2), to which the end collimators are aligned.

The linear relationship shown above may provide focal spot position that can be used for focal spot motion correction. Also, the linear relationship shown above may provide a normalization reference that tracks the intensities of the moving focal spot.

For example, the calibration method, for the normalization reference that tracks the intensities of the moving focal spot, includes measuring a Ratio_1 at one know focal spot, such as the first focal spot position (e.g., the focal spot 102 or 206 in FIGS. 1 and 2) and measuring a Ratio_2 at a second focal spot position. After measuring the two ratios, a ratio can be used to fit the curve and calculate calibration coefficients a and b.

It should be noted that gain, for focal spot motion correction, may be calculated using a function where the focal spot position is the main variable, for example, as follows:

Gain Scaling Factor $K$=Function(fsp)=$1+k_1 \cdot \text{fsp} + k_2 \cdot \text{fsp}^2 +$ The focal spot position (fsp) vs, view (v) is described as:

$$fsp(v) = \frac{(\text{Ratio}(v) - b)}{a}$$

$$\text{Ratio}(v) = \frac{I_{ch=1}(v)}{I_{ch=M}(v)}$$

or $$\frac{I_{ch=1}(v) + I_{ch=2}(v)}{I_{ch=M-1}(v) + I_{ch=M}(v)}$$

where M may be the last end channel in the collimator/detector assembly.

Figure 7:
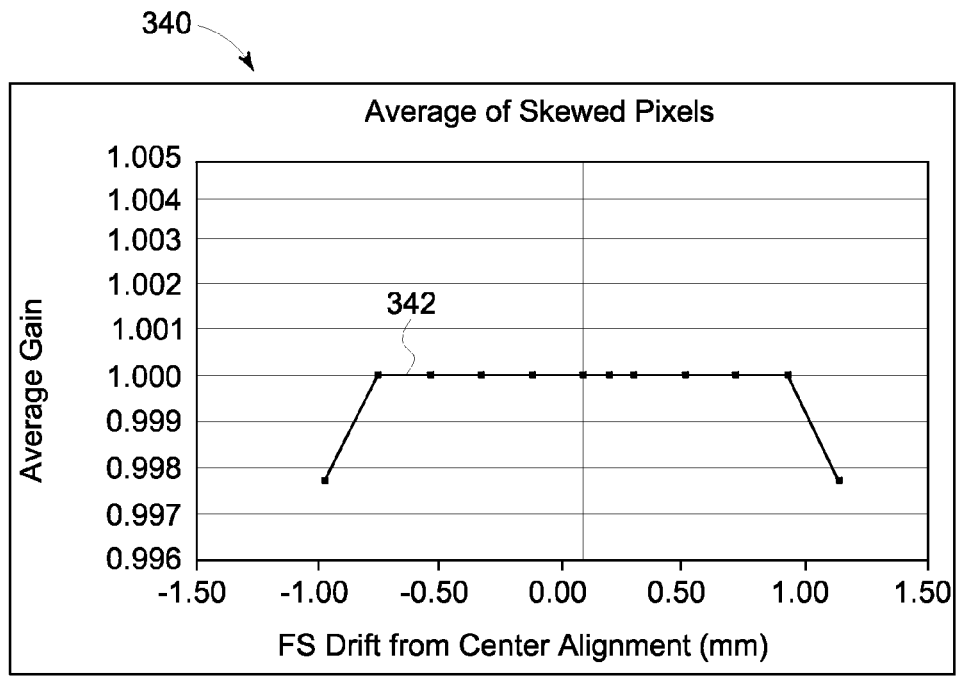
FIG. 7 is a graph illustrating the relationship of average gain and focal spot drift with focal spot tracking in accordance with an embodiment.

FIG. 7 is a graph 340 illustrating the relationship of average gain and focal spot drift (using the line 342) with focal spot tracking in accordance with an embodiment. In particular, the graph 340 illustrates the relationship of average gain and focal spot drift calculated using two end detectors with the collimators focused to a virtual focal spot. For example, the two detectors are oppositely misaligned from the real focal spot position as described herein. The reference channels may be represented as:

$I_{ref} = [I_{(ch=1)} + I_{(ch(M))}]/2$ or $I_{ref} = [I_{(ch=1)} + I_{(ch=2)} + I_{(ch=M-1)} + I_{(ch(M))}]/4$ The reference channel is equal to the average of two oppositely skewed channels and is independent of the focal spot position (fsp). Accordingly, correction for focal spot motion may be performed by measuring for every view, a Ratio (v) and then calculating fsp.

Figure 8:
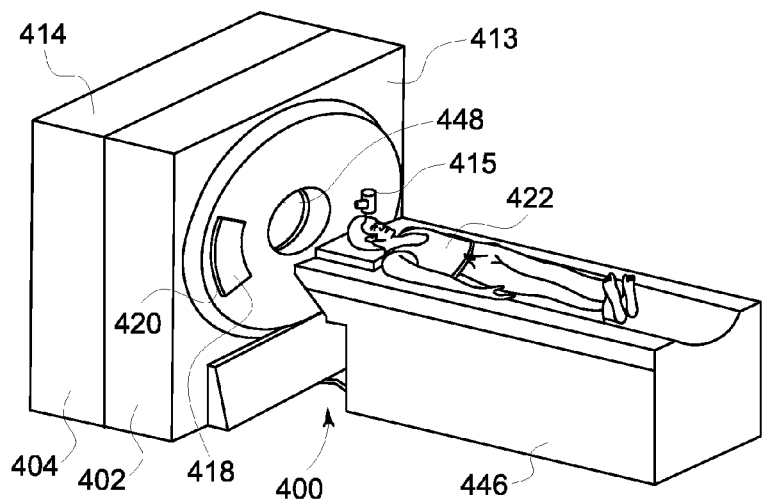
FIG. 8 is a perspective view of an exemplary imaging system that may be configured to implement the various embodiments.
Figure 9:
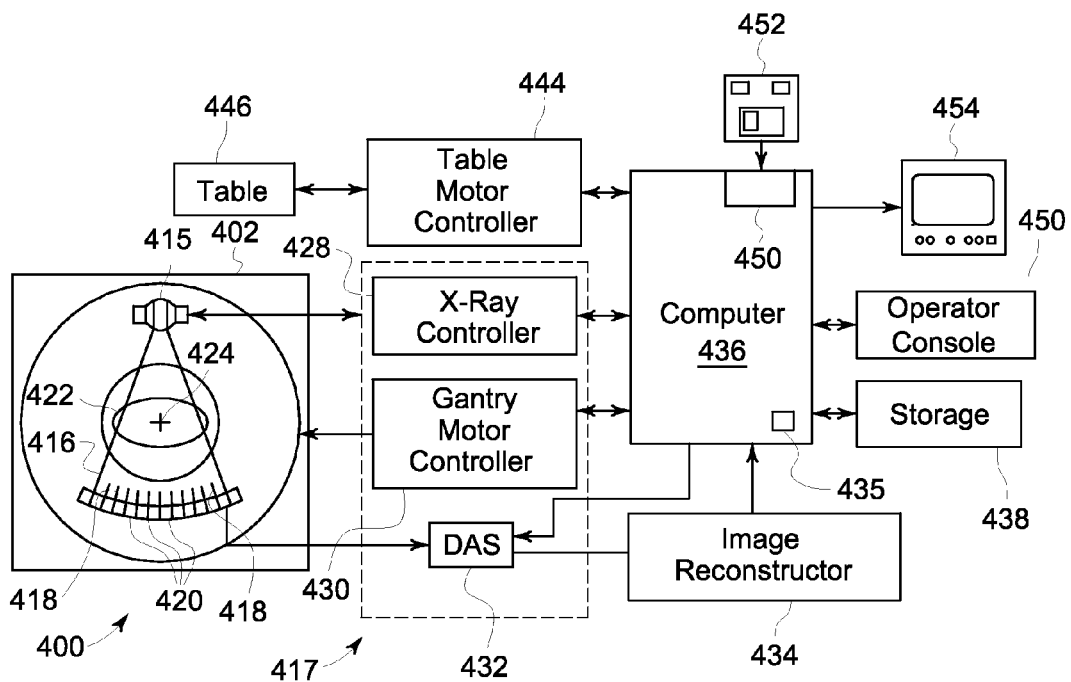
FIG. 9 is a schematic block diagram of the imaging system shown in FIG. 8.

Additionally, normalization of every channel to the aligned position may be performed using the correction I(ch)_corr=I(ch)_meas/Scale_Factor(ch) where: Scale_Factor=1+ k1*fsp+k2*fsp2+ . . . where k1 and k2 are coefficients determined during detector calibration FIG. 8 is a perspective view of an exemplary imaging system 400 that may be configured to implement the various embodiments described herein. FIG. 9 is a schematic block diagram of the imaging system 400 (shown in FIG. 8). In the exemplary embodiment, the imaging system 400 is a multi-modal imaging system and includes a first modality unit 402 and a second modality unit 404. The modality units 402 and 404 enable system 400 to scan an object, for example, the subject 422, in a first modality using the first modality unit 402 and to scan the subject 422 in a second modality using the second modality unit 404. The system 400 allows for multiple scans in different modalities to facilitate an increased diagnostic capability over single modality systems.

In one embodiment, the multi-modal imaging system 400 is a Computed Tomography/Positron Emission Tomography (CT/PET) imaging system 400. The CT/PET system 400 includes a first gantry 413 associated with the first modality unit 402 and a second gantry 414 associated with the second modality unit 404. In other embodiments, modalities other than CT and PET may be employed with imaging system 400.

A plurality of collimators 418 is provided with a plurality of detectors 420 to form units or modules. The plurality of collimators 418 positioned between the subject 422 and the plurality of detectors 420, wherein one or more collimators 418 at the left end of the plurality of collimators 418 and one or more of the collimators at the right end of the plurality of collimators 418 are aligned to a different focal spot than the other collimators 418 as described herein. In one embodiment, the collimators at the left end of the plurality of collimators 418 and the collimators at the right end of the plurality of collimators 418 include only two collimators (one at each end).

The imaging system 400 forms an image region from which the detectors 420 (which may form a detector array) contribute intensity information for image reconstruction. In one embodiment, the collimators 418 at the left end of the plurality of collimators 418 and the collimators 418 at the right end of the plurality of collimators 418 are within the imaging region as described herein. Alternatively, the collimators 418 at the left end of the plurality of collimators 418 and the collimators 418 at the right end of the plurality of collimators 418 are outside the imaging region.

Thus, the plurality of collimators 418 are aligned to a focal spot different than the a focal spot to which the collimators 418 at the left of the plurality of collimators 418 end and the collimators 418 at the right end of the plurality of collimators 418 are aligned. In one embodiment, the collimator(s) 418 at the left end of the plurality of collimators 418 and the collimator(s) 418 at the right end of the plurality of collimators 418 are skewed by a fixed angle in opposite directions (which may be a physical skewing).

The collimator(s) 418 at the left end of the plurality of collimators 418 and the collimator(s) 418 at the right end of the plurality of collimators 418 in some embodiments are configured to measure focal spot motion. Also, the radiation received by the detectors 420 at the collimators 418 at the left end of the plurality of collimators 418 and the collimators 418 at the right end of the plurality of collimators 418 may be used to normalize detector gain for the plurality of detectors 420.

The gantry 413 includes the first modality unit 402 that has an x-ray source 415 that projects a beam of x-rays 416 towards the detectors 420 on the opposite side of the gantry 413. The detectors 420 may be formed by a plurality of detector rows (not shown) including a plurality of detector elements that together sense the projected x-rays that pass through an object, such as the subject 422. Each of the detector elements of the detectors 420 produces an electrical signal that represents the intensity of an impinging x-ray beam and therefore, allows estimation of the attenuation of the beam as it passes through the subject 422.

During a scan, to acquire x-ray projection data, the gantry 413 and the components mounted thereon rotate about an examination axis 424. FIG. 9 shows only a single row of detector elements (i.e., a detector row). However, the detectors 420 may be configured as a multislice detector array having a plurality of parallel detector rows of detector elements such that projection data corresponding to a plurality of slices can be acquired simultaneously during a scan. It should be noted that operation of the second modality unit 404 with the gantry 414 may be provided similarly.

The rotation of the gantry 413, and the operation of x-ray source 415, are controlled by a system controller 417 of the CT/PET system 400. The system controller 417 includes an x-ray controller 428 that provides power and timing signals to the x-ray source 415 and a gantry motor controller 430 that controls the rotational speed and position of the gantry 413. A data acquisition system (DAS) 432 of the system controller 417 samples data from detectors 420 for subsequent processing as described above. An image reconstructor 434 receives sampled and digitized x-ray projection data from the DAS 432 and performs image reconstruction. The reconstructed image is transmitted as an input to a computer 436 that stores the image in a storage device 438. The computer 436 may be programmed to implement the various embodiments described herein. More specifically, the computer 436 may include an image processing module 435 that is programmed to carry out the various methods described herein (e.g., collimator skewing operations).

The computer 436 also receives commands and scanning parameters from an operator via an operator workstation or console 450 that has an input device, such as, keyboard. An associated display 454 allows the operator to observe the reconstructed image and other data from the computer 436. The operator supplied commands and parameters are used by computer 436 to provide control signals and information to the DAS 432, the system controller 417, and the gantry motor controller 430. In addition, the computer 436 operates a table motor controller 444 which controls a motorized table 446 to position the subject 422 in the gantry 413 or 414. Specifically, the table 446 moves portions of the subject 422 through a gantry opening 448.

In one embodiment, the computer 436 includes a read/write device 452, for example, a floppy disk drive, CD-ROM drive, DVD drive, magnetic optical disk (MOD) device, or any other digital device including a network connecting device such as an Ethernet device for reading instructions and/or data from a non-transitory computer-readable medium, such as a floppy disk, a CD-ROM, a DVD or another digital source such as a network or the Internet, as well as yet to be developed digital means. In another embodiment, the computer 436 executes instructions stored in firmware (not shown). The computer 436 is programmed to perform functions as described herein, and as used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein. The CT/PET system 400 also includes a plurality of PET detectors (not shown) including a plurality of detector elements forming part of the second modality unit 404.

Various embodiments described herein provide a tangible and non-transitory machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

Figure 10:
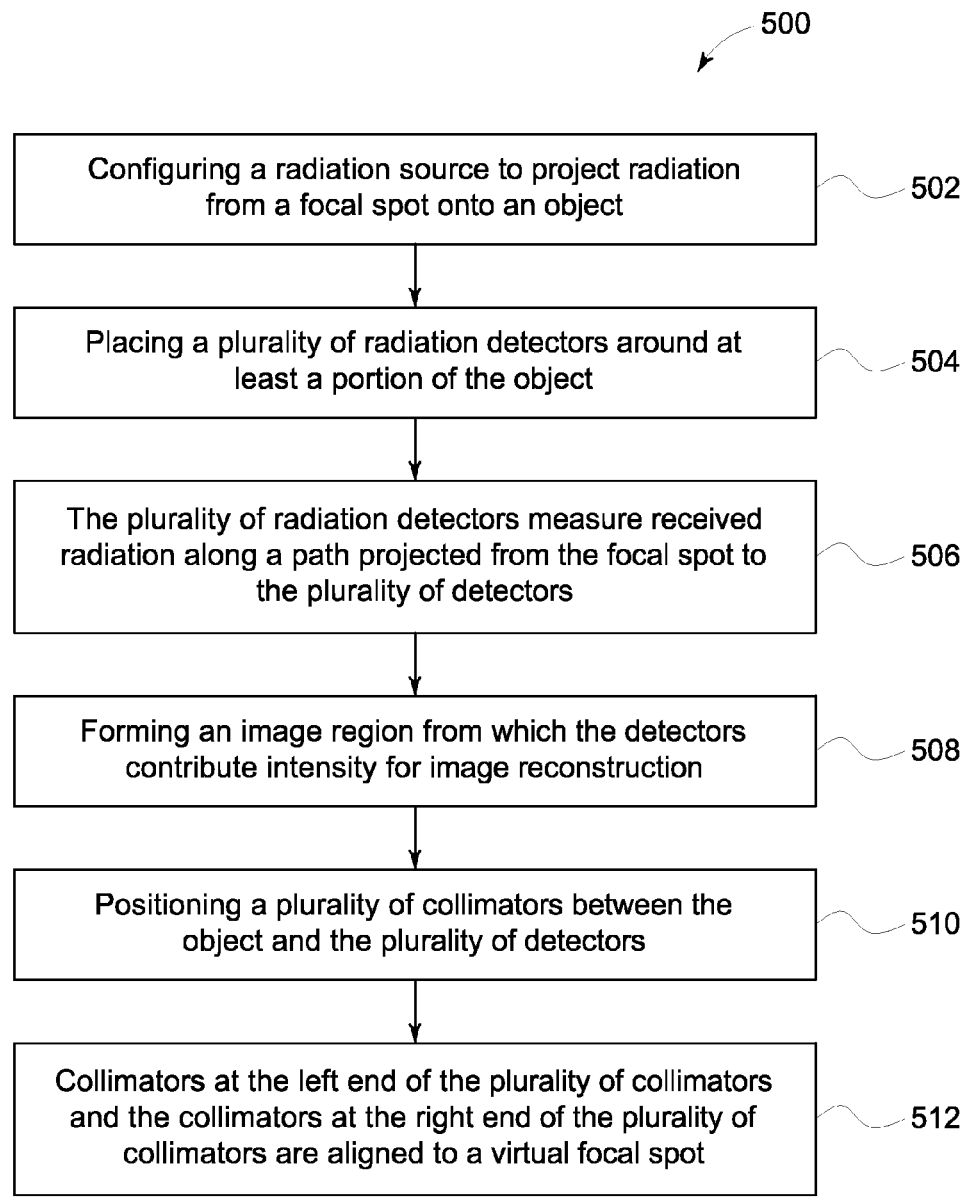
FIG. 10 is a flowchart of a method to track a focal spot in accordance with an embodiment.

The various embodiments may provide a method 500 as shown in FIG. 10 to track focal spot motion, such as the position of a focal spot. The method 500 may be used to sensitize an imaging system to focal spot motion. The method 500 includes at 502 configuring a radiation source to project radiation from a focal spot onto an object. For example, the radiation source may be any radiation source that project electromagnetic waves.

A plurality of radiation detectors are placed around at least a portion of the object at 504. The plurality of radiation detectors placed around the object are configured to measure received radiation at 506 along a path projected from the focal spot to the plurality of detectors. At 508, the plurality of detectors are further configured to form or define an imaging region. The imaging region may be a region from which the detectors detect the incoming radiation to produce intensity information that may be used to produce an image.

Then at 510, a plurality of collimators are positioned between the object and the plurality of detectors. The plurality of collimators provide channels for the radiation originating from a first focal spot to pass to the detectors. Also, the plurality of collimators in an imaging system protect the detectors from receiving the background radiation that may add noise to the images generated using the imaging system.

At 512, the collimators at the left end of the plurality of collimators and the collimators at the right end of the plurality of collimators are aligned to a second focal spot different than the first focal spot. In one embodiment, the second focal spot may be below the first focal spot. Optionally, the second focal spot may be above the first focal spot. In one embodiment, the collimators at the left end of the plurality of collimators and the collimators at the right end of the plurality of collimators include only two collimators.

In an alternate embodiment, the collimators at the left end of the plurality of collimators and the collimators at the right end of the plurality of collimators are within the imaging region. Optionally, the collimators at the left end of the plurality of collimators and the collimators at the right end of the plurality of collimators are outside the imaging region. Thus, the plurality of collimators are aligned to the first focal spot, which may be any focal spot other than the focal spot to which the collimators at the left of the plurality of collimators end and the collimators at the right end of the plurality of collimators that are aligned (namely the second focal spot).

Optionally, the collimators at the left end of the plurality of collimators and the collimators at the right end of the plurality of collimators are skewed by a fixed angle in opposite directions. For example, the collimators at the left end of the plurality of collimators are skewed or defocused by plus three minutes and the collimators at the right end of the plurality of collimators are skewed by minus three minutes.

The non-skewed or non-defocused collimators may be configured to measure the first focal spot motion wherein the first focal spot may be the actual focal spot. Also, the radiation received by detectors at the collimators at the left end of the plurality of collimators and the collimators at the right end of the plurality of collimators may used to measure the second focal spot, as well as to normalize detector gain for the plurality of detectors.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from its scope. While the dimensions, types of materials and coatings described herein are intended to define the parameters of the various embodiments, the various embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English eqivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An imaging system comprising:
   a radiation source configured to project radiation from a first focal spot onto an object;
   a plurality of radiation detectors disposed around at least a portion of the object, wherein the plurality of radiation detectors measure received radiation along a path projected from the first focal spot to the plurality of detectors;
   an imaging region from which the detectors provide image information for image reconstruction; and
   a plurality of collimators positioned between the object and the plurality of radiation detectors, wherein at least one collimator at a first end of the plurality of collimators and at least one collimator at a second end of the plurality of collimators are aligned to a second focal spot different than the first focal spot and having a different location, wherein the collimators at the first end and the second end of the plurality of collimators are physically skewed by a fixed angle in opposite directions that is defocused from the first focal spot.

2. The imaging system of claim 1, wherein the collimators at the first end and the second end of the plurality of collimators comprise two collimators.

3. The imaging system of claim 1, wherein the collimators at the first end and the second end of the plurality of collimators are within the imaging region.

4. The imaging system of claim 1, wherein the collimators at the first end and the second end of the plurality of collimators are outside of the imaging region.

5. The imaging system of claim 1, wherein the plurality of collimators, other than the collimators at the first end and second end of the plurality of collimators, are aligned to the first focal spot.

6. The imaging system of claim 1, wherein the collimator at the first end of the plurality of collimators is skewed by an angle of plus three minutes and the collimator at the second end of the plurality of collimators is skewed by an angle of minus three minutes.

7. The imaging system of claim 1, wherein the collimators at the first end the second end of the plurality of collimators measure only focal spot motion.

8. The imaging system of claim 1, wherein the radiation received by radiation detectors at the collimators at the first end and the second end of the plurality of collimators is used to normalize detector gain for the radiation detectors.

9. The imaging system of claim 1, wherein the radiation source projects electromagnetic waves.

10. A method to track focal spot motion, the method comprising:
    configuring a radiation source to project radiation from a first focal spot onto an object;
    configuring a plurality of radiation detectors to surround at least a portion of the object, wherein the plurality of radiation detectors measure received radiation along a path projected from the first focal spot to the plurality of detectors, wherein an imaging region from which the detectors contribute intensity for image reconstruction is defined; and
    providing a plurality of collimators between the object and the plurality of radiation detectors, wherein at least one collimator at a first end of the plurality of collimators and at least one collimator at a second end of the plurality of collimators are aligned to a second focal spot, wherein the first focal spot is different than the second focal spot; and
    using the radiation received by radiation detectors at the collimators at the first end and the second end of the plurality of collimators to normalize detector gain for the radiation detectors.

11. The method of claim 10, wherein the collimators at the first end of the plurality of collimators and the second end of the plurality of collimators are within the imaging region.

12. The method of claim 10, wherein the collimators at the first end and the second end of the plurality of collimators are outside the imaging region.

13. The method of claim 10, wherein the plurality of collimators, other than the collimators at the first end and the second end of the plurality of collimators, are aligned to the first focal spot.

14. The method of claim 10, further comprising physically skewing the collimators at the first end and the second end of the plurality of collimators by a fixed angle in opposite directions.

15. The method of claim 10, further comprising skewing the collimator at the first end of the plurality of collimators by an angle of plus three minutes and skewing the collimator at the second end of the plurality of collimators by an angle of minus three minutes.

16. The method of claim 10, further comprising configuring the collimators at the first end and the second end of the plurality of collimators measure only focal spot motion.

17. The method of claim 10, wherein the radiation source projects electromagnetic waves.

18. A non-transitory computer readable storage medium for tracking a focal spot of a detector using a processor, the non-transitory computer readable storage medium including instructions to command the processor to realign the collimation of at least one collimator at a first end of a plurality of collimators and at least one collimator at a second end of the plurality of collimators, such that the collimators at the first and second ends are aligned to a focal spot different than the other ones of the plurality of collimators, the non-transitory computer readable storage medium including instructions to command the processor to use the radiation received by radiation detectors at the collimators at the first end and the second end of the plurality of collimators to normalize detector gain for radiation detectors at the other ones of the plurality of collimators.

19. The imaging system of claim 1, wherein each of the plurality of collimators is configured to define a channel through which radiation from the radiation source is directed to at least one of the plurality of radiation detectors.

20. The imaging system of claim 1, wherein at least one detector associated with at least one of the at least one collimator at the first end or the at least one collimator at the second end is aligned with second focal spot.

21. The imaging system of claim 1, wherein at least one detector associated with at least one of the at least one collimator at the first end or the at least one collimator at the second end is aligned to receive about 90% of the radiation that the at least one detector would receive if the at least one detector were aligned with the first focal spot.

22. The method of claim 10, wherein each of the plurality of collimators is configured to define a channel through which radiation from the radiation source is directed to at least one of the plurality of radiation detectors.

23. The method of claim 10, wherein at least one detector associated with at least one of the at least one collimator at the first end or the at least one collimator at the second end is aligned to receive about 90% of the radiation that the at least one detector would receive if the at least one detector were aligned with the first focal spot.

24. The method of claim 10, wherein each of the plurality of collimators is configured to define a channel through which radiation from the radiation source is directed to at least one of the plurality of radiation detectors.

* * * * *